(12) United States Patent
Johnson

(10) Patent No.: US 10,294,608 B2
(45) Date of Patent: May 21, 2019

(54) FABRIC TREATMENT METHOD

(71) Applicant: Sciessent LLC, Wakefield, MA (US)

(72) Inventor: Kenneth T. Johnson, Swampscott, MA (US)

(*) Notice: Subject to any disclaimer, the term of this patent is extended or adjusted under 35 U.S.C. 154(b) by 396 days.

(21) Appl. No.: 14/855,413

(22) Filed: Sep. 16, 2015

(65) Prior Publication Data
US 2016/0083900 A1  Mar. 24, 2016

Related U.S. Application Data

(60) Provisional application No. 62/052,782, filed on Sep. 19, 2014.

(51) Int. Cl.

| *A01N 25/10* | (2006.01) |
|---|---|
| *A01N 25/34* | (2006.01) |
| *A01N 59/16* | (2006.01) |
| *A01N 59/20* | (2006.01) |
| *D06M 11/50* | (2006.01) |
| *D06M 11/57* | (2006.01) |
| *D06M 11/83* | (2006.01) |

(52) U.S. Cl.
CPC .......... *D06M 11/83* (2013.01); *A01N 59/16* (2013.01); *A01N 59/20* (2013.01); *D06M 11/50* (2013.01); *D06M 11/57* (2013.01)

(58) Field of Classification Search
CPC .. B32B 5/02; B32B 27/04; C11D 3/00; B21B 1/46; D06M 11/83; D06M 11/57; D06M 11/50; A01N 59/16; A01N 59/20
See application file for complete search history.

(56) References Cited

U.S. PATENT DOCUMENTS

| 6,584,668 | B2 | 7/2003 | Green et al. |
|---|---|---|---|
| 6,764,969 | B1 | 7/2004 | Kuhn et al. |
| 6,979,491 | B2* | 12/2005 | Yan ...................... D02G 3/449 |
| | | | 106/1.13 |
| 7,291,570 | B1 | 11/2007 | Green et al. |
| 8,394,392 | B2 | 3/2013 | Imahashi et al. |
| 2002/0083534 | A1* | 7/2002 | Wang ...................... C09B 49/00 |
| | | | 8/650 |
| 2009/0047311 | A1* | 2/2009 | Imahashi .............. A01N 59/16 |
| | | | 424/401 |
| 2010/0215871 | A1 | 8/2010 | Nilitz et al. |
| 2011/0065346 | A1 | 3/2011 | Bender et al. |

FOREIGN PATENT DOCUMENTS

| CN | 100547149 C | 10/2009 | |
|---|---|---|---|
| EP | 1905303 A1 * | 4/2008 | ............ A01N 59/16 |
| WO | 01/94687 A2 | 12/2001 | |

OTHER PUBLICATIONS

Matthew Henry, "Advances in Odor Control Technologies for Textiles," NanoHorizons, Inc., AATCC Conference presentation Sep. 16-17, 2015.
Dave Klein, "Topical Applications of Antimicrobials," Thomson Research Associates, AATCC Conference presentation Sep. 16-17, 2015.
K. Mark Wiencek, "AgZrP: With This Silver, It's All About the Cube," Milliken, AATCC Conference presentation Sep. 16-17, 2015.
Steve Cunningham, "Dual Functionality: The Key to Effective Odor Control in Textiles," Sciessent, LLC, AATCC Conference presentation Sep. 16-17, 2015.
International Search Report and Written Opinion for PCT/US15/51103.
Ghaheh, FS et al., "Assessment of antibacterial activity of wool fabrics dyed with natural dyes", Journal of Cleaner Production 72 (2014) pp. 139-145.
European Patent Office Extended Search Report dated May 4, 2018.

* cited by examiner

*Primary Examiner* — Gregory R Delcotto
*Assistant Examiner* — Preeti Kumar
(74) *Attorney, Agent, or Firm* — IP&L Solutions; Edward K Welch, II

(57) ABSTRACT

A method for treating a sulfur-containing fabric and sulfur-containing fabrics with excellent antimicrobial properties are disclosed. First an aluminum salt is added to a sulfur-containing fabric. That product is then rinsed. The rinsed product is combined with an antimicrobial. In one embodiment, the sulfur-containing fabric is combined with an aqueous solution of an oxidizing agent prior to the addition of the aluminum salt. Fabrics treated by the method retain excellent antimicrobial activity even after repeated washings.

21 Claims, No Drawings

FABRIC TREATMENT METHOD

RELATED APPLICATION

The present application claims the benefit of U.S. Provisional Patent Application No. 62/052,782 entitled Fabric Treatment Method filed on Sep. 19, 2014, the contents of which are incorporated herein in total by reference.

FIELD OF THE INVENTION

The invention relates to a method for treating a fabric that is particularly useful for imparting wash durable antimicrobial and/or anti-odor properties to fabrics.

BACKGROUND OF THE INVENTION

For more than a decade now a great deal of attention has been focused on the hazards of bacterial, fungal, and viral contamination from everyday exposures. What once was a primary concern for health care facilities, especially hospitals, and food processing/food preparation facilities, is now an everyday concern for most every business, the home, schools, public transportation and so on. More virulent and, oftentimes, drug resistant strains of pathogenic bacteria are being identified around the globe. And, while such issues were once considered localized issues, they are now regional, nationwide, if not world-wide issues owing to the ease and extent to which the people of the world travel, not to mention the world-wide market place for manufactured goods and, perhaps more critically, produce and other foodstuff.

While pathogenic bacteria are certainly a major concern, they are not the only concern. The world is flush with microorganisms that may not cause death or sickness; yet they impose upon or adversely impact our lives on a daily basis. For example, molds can create an unsightly appearance in or on our homes, especially in bathrooms and basements; certain bacteria may affect the smell and/or taste of our drinking water, other bacteria affect the smell of clothing, towels, upholstery and other fabrics, etc.

Numerous efforts have been undertaken to ward off contamination and/or transmission of such bacteria, fungi and other microorganisms. Specifically, much effort has been made to introduce antimicrobial performance into a host of specialized and non-specialized products and articles of manufacture, especially those comprising or associated with touch surfaces. Such products and articles run the gamut, from cutting boards to refrigerator linings, from door knobs to cellular telephone housings, from HVAC units and components to medical devices such as stents, catheters and the like, from fabrics to wound care products, etc. This antimicrobial performance is achieved by either treating the surface of the product or article with a coating containing an antimicrobial agent or directly incorporating the antimicrobial agent into the material or composition from which the product or article is made.

While many of these applications have achieved varying degrees of commercial and technical success, one particular application, fabrics, especially for apparel, has and continues to be an area of continual developmental effort. Early on, manufacturers employed organic antimicrobial agents, most frequently triclosan, as an antimicrobial agent applied as a topical treatment or, more commonly, incorporated into the polymer melt from which the fibers/filaments are spun/extruded. However, the ability to incorporate triclosan into fiber materials is limited: showing success in acrylic and/or acetate fibers but not in polyamides, polyesters, etc. The use of triclosan has also raised certain health and safety concerns, especially with respect to skin irritation and sensitivity to the chlorine and chlorides within these compounds as well as the possible bioabsorption of the triclosan and/or its components/degradation residues into the body. Furthermore, triclosan has poor longevity in these applications due to its mobility in polymer compositions and the quickness with which it is washed out of the fabric.

The antimicrobial properties of a number of inorganic materials, especially metals such as silver, copper, zinc, mercury, tin, gold, lead, bismuth, cadmium, chromium and thallium, have long been known. Certain of these metals, especially silver, zinc, gold and copper, have enjoyed greater success due to their relatively low environmental and toxicological effects and high antimicrobial activity. In order to address some of the aforementioned problems with organic antimicrobial agents like triclosan, others have taken the approach of coating fibers, filaments and/or fabric with silver metal by, for example, vapor deposition or other plating techniques. These methods bind the silver metal to the surface of the polymer fiber/filament. Antimicrobial performance arises from the relatively slow oxidation of the surface of the silver metal and the subsequent availability/release of antimicrobially active silver ions from the oxidized silver. Although effective and long lived, antimicrobial performance is poor to marginal owing to the slow rate at which the silver ions are generated: effectiveness being a function of the extent of ion generation and, hence, the rate of oxidation.

Further compounding the efficacy of silver metal is that fact that washing of the substrate or substrate surface removes all or substantially all of the oxidized silver. Consequently antimicrobial efficacy following washing is delayed until a sufficient level of oxidation or other generation of silver ions occurs on the surface of the silver metal coating Speed of oxidation is not the only concern; the costs of these silver coated materials are relatively high—though one can regulate the costs, at the expense of performance, by using less silver coated fiber in the fabric. Furthermore, fabrics made with these materials oftentimes have associated therewith a static nuisance owing to the electrical conductivity of the silver fibers. Finally, as would be expected, the presence of the silver coated fibers affects the color and feel of the fabric. Since these fibers do not absorb the dyes used to color the fabric, they will always stand out. The degree of their impact on the color or visual image depends upon the content of silver coated fiber in the fabric.

In an effort to address many of the aforementioned consequences and shortcomings of silver metal and organic antimicrobial agents, recent attention has been focused on the use of certain inorganic silver compounds, complexes and the like. Suitable inorganic silver antimicrobial agents may take many different forms including simple silver salts or complexes including wholly inorganic salts as well as organometallic complexes. Other, and especially beneficial, complex forms include those antimicrobial agents comprising ceramic particles having ion-exchanged silver ions carried therein or thereon as well as water soluble glasses that have incorporated therein various readily soluble silver ion sources. Exemplary ion-exchange type antimicrobial agents include those wherein the ion-exchange carrier particles are ceramic particles including zeolites, hydroxy apatites, zirconium phosphates and the like. Antimicrobial agents based on zeolite carriers are disclosed in, for example, U.S. Pat. Nos. 4,911,898; 4,911,899; 4,938,955; 4,906,464; and 4,775,585. Antimicrobial zirconium phosphates include those disclosed in, for example, U.S. Pat. Nos. 4,025,608 and 4,059,679 and the Journal of Antibacterial Antifungal Agents Vol. 22, No. 10, pp. 595-601, 1994. Finally, antimicrobial hydroxyapatites powders include those disclosed in U.S. Pat. Nos. 5,009,898 and 5,268,174, among others.

Although these antimicrobial agents have found growing success in the production of antimicrobial fabrics and enable excellent antimicrobial performance, generally without the delay of the silver metal coated fibers, they still have some of the same shortcomings as well as some additional problems. For example, except for hydrophilic polymers, when the antimicrobial agent is incorporated into the original polymer material from which the fiber or fabric is made, only that portion of the antimicrobial agent at or proximate to the surface of the fiber or filament made thereof is available to provide antimicrobial efficacy. Specifically, because these agents rely upon contact with water or moisture to release and transport the antimicrobial silver ion, unless there are pores in the polymer or the polymer has hydrophilic characteristics, there are no transport pathways for the ions from within the polymer Consequently, with hydrophobic or insufficiently hydrophilic amphiphilic materials, the manifestation of antimicrobial efficacy is limited to those antimicrobial agents in contact with the surface of the fibers. Thus, depending upon the denier of the fibers, there is the possibility that much of the antimicrobial agent may be wasted and non-accessible, thereby adding costs without benefit. Of course, this detriment is mitigated somewhat in those fabrics which are employed in applications that are subject to wear because the erosive effect of wear will expose previously entombed antimicrobial agent. But, then again, wear also means that the integrity of the fiber itself, especially its strength and, in clothing, insulating property and appearance will be adversely affected. While the issue of longevity is less of a concern for "single-use" disposable type articles or infrequently laundered articles such as curtains, upholstery, etc., it is especially critical and of concern for fabrics used in apparel that is likely to be washed quite frequently, if not following each use. Regardless, antimicrobial efficacy is limited inasmuch as only those antimicrobial metal ion sources that are exposed are available to provide antimicrobial metal ions for antimicrobial performance. This compares with those fibers, filaments and the like that are made with sufficiently hydrophilic polymers which enable ion transport from within and throughout the fiber material. Here, all of the antimicrobial agent, even that entombed within the polymer, is available to contribute ions to antimicrobial performance. Thus, less antimicrobial agent is required to achieve the same level of efficacy in hydrophilic materials as compared to hydrophobic or insufficiently hydrophilic amphiphilic materials.

Another shortcoming of the inorganic silver antimicrobial agents, particularly those comprising the simple silver salts and other highly soluble silver antimicrobial agents, is their short-lived nature. Because of the limited amount of antimicrobial agent at the surface, a high degree of solubility means that the full amount of antimicrobial active at the surface can quickly be washed away or otherwise depleted. In hydrophilic materials, some of this loss is mitigated by ion transport of ions from within the polymer: though transport, and hence release, is limited by the rate of ion transport. And, as noted above, in all applications, those fibers that are subject to wear will seemingly replenish as the entombed antimicrobial agent is exposed at the surface of the fibers and filaments; however, again, that which is newly exposed is quickly depleted as well. Furthermore, because wear is not typically even, replenishment only affects those areas subject to constant wear. Thus, in the absence of a constant and even wear, which also means limited life to the fabric; antimicrobial efficacy slowly lessens over time as the exposed antimicrobial source is depleted.

In following, degree of performance and longevity of performance, especially as relates to wash-durability, have long been of notable concern. Numerous efforts have been undertaken and incremental advances have been made to address these issues. U.S. Pat. No. 6,607,994 points out that fabric treatments endowing particular characteristics or activity are highly desired by the apparel, home furnishings, and medical industries but conventional processes used to impart such characteristics often do not lead to permanent effects. Laundering or wearing of the treated fabric causes leaching or erosion of the agents responsible for imparting the desired characteristics. Attempts to address the problem by using encapsulated nanoparticles that form covalent bonds to the fabric have had limited success and, besides, functionalizing the nanoparticles and then chemically bonding them to the fabric adds complexity and cost and is not suitable for most applications, particularly not for broad scale consumer application in, e.g., clothing, bedding, upholstery, and the like.

Trogolo et. al., U.S. Pat. No. 6,436,422, employed hydrophilic polymer coatings so as to enhance longevity by ensuring that all of the antimicrobial agent within the coating is available for providing antimicrobial efficacy. However, hydrophilic polymer fibers and hydrophilic polymer coated fibers have limited use due to the relatively poor physical and performance properties of the hydrophilic polymer materials themselves.

Hendriks et al., U.S. Pat. No. 7,754,625, made improvements in wash durability by using an antimicrobial agent that combined a water-soluble zinc salt such as zinc oxide, and an antimicrobial metal ion source of silver and copper ions. They tested white polyester fabric and focused on discoloration of the fabric. The samples showed good bio-efficacy even after several wash cycles. This represented significant progress towards the problem but, it turns out, was not universal and encounters issues with certain fabrics and/or dyed fabrics.

Specifically, it has now been found that certain chemicals or species of chemicals that are inherently present in fibers or that are incorporated and/or applied to fibers and fabrics have an adverse effect on ionic antimicrobial metals. In this regard, it is uncommon for a fabric not to be subjected to some treatment either prior to or after incorporation into an article of manufacture. Common treatments include dyes, sizings, etc. Dying is perhaps the most common treatment with sulfur dyes and indigo a couple of the most widely used dyes. Sulfur dyes are so named because of the use of sulfur in their synthesis. They are commonly used in the dying of cellulosic materials, especially cotton, and are typically associated with dark colors such as blacks, browns and deep blues. C.I. Sulfur Black 1 is an example of a sulfur dye. Denim, perhaps one of the most ubiquitous fabrics of the day, is typically dyed with indigo, alone, or more commonly, with both indigo and a sulfur dye. Due to growing concerns with the use of indigo dyes, especially from an environmental perspective, sulfur dyes are becoming even more critical and prolific in the dying of denim with sulfur dyes soon expected to surpass indigo as the key denim dye.

Although desirable and, oftentimes, necessary such treatments can further complicate the ability to impart antimicrobial activity to fabrics and articles made therefrom. Specifically, these treatments are found to contain chemical compounds which or whose degradation or oxidation products interfere with the antimicrobial agent, oftentimes chemically binding the metal ions so as to render them unavailable for antimicrobial performance. This is especially so with sulfur containing treatments, especially sulfur dyes. Although its exact mechanism of action is uncertain, it is believed that the sulfur binds with and/or complexes with the antimicrobial metal ions: thereby negating their antimicrobial efficacy.

However, this issue is not just limited to treated or dyed fabric. Indeed, certain fibers and fabrics, most especially wool and fabrics made of or containing wool, manifest poor, if any, antimicrobial efficacy following treatment with antimicrobial metal ion type antimicrobial agents. Further investigation has found that these fibers, most especially wool, naturally contain chemical compounds or species, particularly sulfur and sulfur containing compounds: thus, suffering the same consequence of dyes and treatments containing like compounds and species.

Thus, while considerable effort has been expended in the development of antimicrobial and anti-odor treatments for fabrics, problems continue. This is especially so for fabrics that are treated with and/or otherwise contain sulfur, especially sulfur dyes.

Thus, there remains a need in the industry for a fabric that provides long lasting antimicrobial and/or anti-odor performance, especially such performance with wash durability. In particular, there is a need for sulfur containing or treated fabrics that have long term antimicrobial and/or anti-odor properties which are not compromised or, if compromised, are minimally compromised by washing, particularly repeated washing There also remains a need for a method, especially a simple and cost effective method, by which antimicrobial and/or anti-odor properties, particularly long lasting and wash durable antimicrobial and/or anti-odor properties, may be imparted to fabrics.

There especially remains a need for a method, especially a simple and cost effective method, by which antimicrobial and/or anti-odor properties, particularly long lasting and wash durable antimicrobial and/or anti-odor properties, may be imparted to sulfur containing and/or sulfur treated fabrics.

SUMMARY OF THE INVENTION

The present teachings pertain to a process for improving the antimicrobial and/or anti-odor performance of fabric whose antimicrobial and/or anti-odor efficacy depends, in whole or in part, upon the release, presence or generation of antimicrobial metal ions, whether through oxidation, degradation, ion-exchange, dissociation, solubilization, and the like.

In a second respect, the present teachings pertain to a process for imparting antimicrobial and/or anti-odor properties to fabrics which have heretofore been found to be incapable of manifesting or manifesting adequate for consumer acceptance antimicrobial and/or anti-odor properties even though the fabrics incorporate and/or have been treated with a typically or otherwise efficacious amount of an anti-microbial and/or anti-odor agent whose efficacy depends, in whole or in part, upon the release, presence or generation of antimicrobial metal ions, whether through oxidation, degradation, ion-exchange, dissociation, solublization, and the like due to an inhibition, interference or interaction with the antimicrobial metal ions.

According to the present teachings, the processes described above entail treating fabrics with one or more compounds which, or whose components or ions, complex with, sequester, bind, and/or react with, most especially preferentially complex with, sequester, bind, and/or react with, compounds or ions that are inherently, including naturally, present in the fabric and/or are imparted to the fabric though some process and/or treatment thereof and which otherwise inhibit the release or generation of, complex with, sequester, bind and/or react with antimicrobial metal ions, particularly in the presence of moisture, e.g., high humidity, washing, swimming, rain, sweating, etc. In a particular embodiment, the present teachings pertain to a process by which fabrics, which inherently or as a result of other treatments, such as dying, contain or have associated therewith sulfur and sulfur compounds, are treated with compounds that complex with, sequester, bind, and/or react with, preferably in a preferential manner as compared to the antimicrobial metal ions, the sulfur or sulfur containing species, especially sulfur containing ionic species.

In its preferred embodiment, the present teaching pertains to a three-step process in which sulfur containing fabrics are treated with an aluminum salt following which the treated material is rinsed/washed with water or other suitable solvent, and, finally, the washed or rinsed material is then treated with an antimicrobial metal ion-type antimicrobial agent. This process is particularly suited for use in the treatment of wool and/or fabrics that have been treated with sulfur dyes, most especially sulfur dyed denim. Preferably, the antimicrobial agent contains a source of silver ions, copper ions, zinc ions or mixtures of any two or all three ions. Optionally, though preferably, the aforementioned processes may further comprise treating the fabric with an oxidizing agent prior to or concurrent with, preferably prior to, the aluminum salt treatment.

In another respect, the present teachings pertain to fabrics that have been treated according the foregoing processes, Most especially, the present teachings pertain to wool and/or fabrics that have been treated with sulfur containing compounds, especially sulfur dyes, which have been treated according to the foregoing processes.

In a preferred embodiment, the present teaching is directed to wool and/or sulfur dye treated fabrics, especially denim, which have been subjected to a three-step process in which the wool or fabric is treated with an aluminum salt following which the treated material is rinsed/washed with water or another suitable solvent, and, finally, the washed or rinsed fabric is then treated with an antimicrobial metal ion-type antimicrobial agent. Optionally, though preferably, the fabric may be subjected to a preconditioning or pretreatment wherein the fabric is treated with an oxidizing agent prior to or concurrent with, preferably prior to, the aluminum salt treatment.

According to yet another aspect, the present teachings pertain to fabrics that have improved antimicrobial and/or anti-odor properties/performance as compared to similar fabrics which have not been subjected to an aluminum salt treatment prior to treatment with an antimicrobial metal ion-type antimicrobial/anti-odor agent.

According to yet another aspect, the present teachings pertain to sulfur containing and/or sulfur treated fabrics which manifest antimicrobial and/or anti-odor properties as a result of the incorporation therein or the treatment thereof with an antimicrobial metal ion-type antimicrobial/anti-odor agent. Most especially, there are provided wool and sulfur dyed fabrics manifesting antimicrobial and/or anti-odor properties as a result of the incorporation therein or the treatment thereof with an antimicrobial metal ion-type antimicrobial/anti-odor agent.

The fabrics processed in accordance with the present teachings provide excellent antimicrobial and/or anti-odor activity which is retained even after repeated washings. Accordingly, and in particular, the present teachings provide for antimicrobial and/or anti-odor sulfur containing or treated fabrics having excellent long term and wash durable antimicrobial and/or anti-odor properties.

DETAILED DESCRIPTION OF THE INVENTION

The invention relates to a method for treating a fabric in order to impart and/or improve antimicrobial and/or anti-odor properties to that fabric. In its most simplest of form the method comprises three key steps. In an alternate embodiment, the method comprises four key steps. Depending upon the final product desired, other steps could be employed as well; however, the aforementioned steps are those necessary for imparting the desired antimicrobial/anti-odor performance to fabrics.

The present invention is applicable to all fabrics. As used in this specification and the claims, the term "fabric" is intended to mean fibers, yarns, cloths, textiles and finished goods made therefrom including apparel, upholstery, etc. The fabric may be woven or non-woven. The fabric may also be made from a variety of synthetic and natural materials and blends thereof. Examples of synthetic materials include nylons, polyesters and polyolefins. Examples of natural materials include wool and cotton. Examples of blends include cotton-polyester, cotton-polyolefin, etc. Preferably, the fabric is cotton. For purposes of convenience, the invention will be described in relation to sulfur containing fabric, most especially denim: though it is to be understood that the teachings are not and are not intended to be so limited. Rather, the present teaching is applicable to any fabric which contains or has associated therewith ions and/or compounds which in the presence of water dissociate to generate ions that have an affinity for antimicrobial metal ions, i.e., they complex with, sequester, bind, and/or react with the antimicrobial metal ions, especially where said affinity leads to a loss and/or absence of antimicrobial and/or anti-odor performance.

By "sulfur-containing", we mean that the fabric contains some form of sulfur. The source of the sulfur can be naturally occurring such as in wool which contains sulfur-containing proteins. The source of the sulfur can also be from additives used in the manufacture and/or treatment of the fabric. For example, the source of the sulfur can be from certain sulfur-containing enzymes used to treat the fabric. A more common source of sulfur in fabrics is sulfur dyes which are used in various amounts and at various stages of fabric manufacture and treatment.

Most preferably the fabric is denim. Denim is a woven fabric formed by interlacing or intermeshing cotton yarns. The direction of weaving is called the "warp" direction, and the cross direction is called the "weft". The weft yarns alternately go over and under the warp yarns. The warp yarn in denim is typically dyed, prior to weaving, with indigo, a naturally occurring blue dye, alone or in combination with a sulfur dye. Indigo dyeing can be performed to various depths of shade ranging from light blue to very dark blue or even black. The added sulfur dye provides additional shading and coloring possibilities to denim. Though still prevalent, indigo dyes are coming under increased pressure due to environmental concerns and, hence, sulfur dyes are gaining importance and use, especially in the dying of denim.

As used herein, when speaking of the load of various antimicrobial metal ions in/on the ceramic carriers and/or their use rates, it is to be noted that the determination is made in terms of the ions as metal: for example, grams of silver ions is determined as grams of silver metal.

Preferably, the fabric employed in the practice of the invention has been dyed. Common dyes include vat dyes and sulfur dyes, alone or in combination. A vat dye is any of a large class of water-insoluble dyes, such as indigo and derivatives of anthraquinone. Commonly, the dye is applied in a soluble, reduced form to impregnate the fiber and then oxidized in the fiber back to its original insoluble form. Vat dyes are especially fast to light and washing. Vat dyes date back several centuries and were so named because of the vats used in the reduction of indigo plants through fermentation.

Sulfur dyes, named because of the use of sulfur in their synthesis, are used, for example, in dark colors such as blacks, browns and deep blues. C.I. Sulfur Black 1, CI Sulfur Brown 12, and CI Sulfur Red 6 are all examples of sulfur dyes. Often, dependent upon the desired color, both indigo and a sulfur dye are used in denim manufacture. Fabrics used in the practice of the present invention have typically, and preferably, been dyed with a sulfur dye or with the combination of indigo and a sulfur dye. Most preferably, the fabric is denim that has been dyed with a sulfur dye, alone or in combination with indigo.

Various dyeing techniques are used. For example, sulfur bottom refers to treatment with sulfur dyes before being dyed with indigo. Sulfur top refers to treatment with sulfur dyes after being dyed with indigo and pure sulfur is when the sulfur dyes are used in the absence of indigo. Indigo itself does not contain sulfur. As a general rule, the amount of sulfur and therefore the difficulties in imparting antimicrobial activity to a fabric Increase from sulfur bottom to sulfur top to pure sulfur.

Optionally, though typically, fabrics to be employed in the practice of the present invention will have undergone other treatments prior to being subjected to the present treatment method. Exemplary treatments include sizing, dyeing and sewing to form garments. They may also have been subject to a desizing treatment wherein sizing, e.g., starch, is removed rather than applied. This is commonly done by treatment with an enzyme which breaks down and releases the sizing agent.

Additionally, especially in the case of denim and other fabrics subjected to a "stressing process," the fabric is often subjected to a stonewashing process. The stonewashing process can use pumice stone, cellulosic enzymes, or sometimes an acid wash and is oftentimes used to give a worn or aged look to the fabric. Many of these prior treatments are done in a vessel washer.

Aluminum Salt Treatment

As noted, in its simplest embodiment, the process employs three steps. The first step involves treating a sulfur-containing fabric with an aluminum salt. Typically the aluminum salt is an aqueous solution of the aluminum salt into which the fabric is placed: though the fabric could be sprayed with the solution as well. Most often, because the present process may be, and preferably is, integrated into and/or immediately follows other fabric treatment processes, especially the dying process, the fabric is treated with the aluminum salt agent in the same vessel, typically a washer, used in the previous treatments. For example, after the fabric is dyed, it is washed to remove excess dye. Once the wash is completed, the aluminum salt solution may be added to the washer containing the fabric or the fabric, if it were first removed, could be added to the washer vessel containing the aluminum salt solution.

Suitable aluminum salts are soluble salts, most especially and preferably water soluble aluminum salts. Exemplary aluminum salts include aluminum sulfates, aluminum phosphates, aluminum hydroxides, aluminum oxides, aluminum halides, and aluminum carboxylates and hydrates of the foregoing as well as mixtures of two or more of the foregoing. Preferred aluminum salts are the carboxylates, especially aluminum citrate and aluminum acetate. Aluminum halides, like aluminum chloride are acceptable, but are less preferred because of possible reactions with water, especially in the case of aluminum chloride. Additionally, the aluminum salt can have a mixture of anionic moieties. For example, the aluminum salt can have both hydroxide and acetate anions as in basic aluminum diacetate, HOAl(AcO)$_2$ or basic aluminum monacetate, (HO)$_2$Al(AcO). The aluminum salt can also have a mixture of cations such as in aluminum potassium sulfate, Alk(SO$_4$)$_2$. Insoluble aluminum salts, such as aluminosilicates and zeolites are not included unless they can be solubilized without adversely affecting the outcome or performance of the claimed process. For example, certain water soluble acids, such as citric acid at appropriate concentrations, will dissolve zeolite; hence a proper aqueous citric acid solution of dissolved zeolite is contemplated. Preferred aluminum salts are aluminum sulfate, aluminum acetate, and aluminum citrate and hydrates thereof. Most preferably, the aluminum salt is hydrated aluminum sulfate because it is gives good results, is readily available and economical.

It is also to be appreciated that the aluminum salt and/or aluminum ions may be generated in-situ or as part of the treatment step. For example, aluminum metal could be treated with an acid, such as hydrochloric acid or, a suitable basic material, such as sodium hydroxide, to dissolve the aluminum metal. Additionally, as mentioned in the previous paragraph, certain insoluble aluminum salts or materials, such as zeolite, can be dissolved in acid solutions to form the aluminum salt. Accordingly, reference herein to aluminum salts is intended to include in-situ formed aluminum salts and in-situ formed salt-forming ions as well.

Preferably, the aluminum salt is dissolved in water prior to being combined with the sulfur-containing fabric. The concentration of aluminum salt in water can vary but is preferably from about 0.1 to about 30% by weight. Lower levels are sometimes less effective and, when too low, ineffective and higher levels add unnecessarily to the cost. More preferably the concentration is from 0.5 to 15% and most preferably from 1 to 10%.

Generally speaking, the aluminum salt is allowed to contact the sulfur-containing fabric for a sufficient period of time to negate the adverse impact of those chemical species, especially sulfur, that interfere with or compromise the performance of the antimicrobial agents and/or the ability to treat fabrics with such antimicrobial agents. Generally, the contact time can vary widely, but is preferably from about one minute to about two hours. Shorter time may give inadequate contact time, thereby enabling some residual interference or degradation with the antimicrobial performance as compared to those fabrics that are treated for a longer period of time. Similarly, longer time, in excess of two hours, may be employed but is believed to be unnecessary and adds time and cost to the process. More preferably, the contact time is from about 10 to about 60 minutes.

Similarly, the temperature at which the aluminum salt treatment is performed may vary widely as well and is typically in the range of from about 10° C. to about 90° C. Cooling or heating, though, add costs and hence it is preferred that the treatment be conducted in the range of from about 20° C. to about 50° C. In essence, the process can be run at room temperature for the production facility in which the treatment is conducted; thereby avoiding unnecessary costs of cooling and heating.

Oxidizing Agent Pretreatment

Optionally, though preferably, one may employ an oxidizing step prior to performing the aluminum salt treatment. It has been found, at least with certain fabrics, that pretreating the fabric with an oxidizing agent prior to performing the aluminum salt treatment facilitates and enhances the effect of the aluminum treatment step. Though not intending to be bound by theory, it is believed that the oxidizing agent oxidizes those species, especially the sulfur, responsible for the interference with the antimicrobial performance rendering them more susceptible to neutralization or binding with the aluminum salt. This step is especially preferred when there are high levels of sulfur in the fabric or when the sulfur is especially accessible because a sulfur dye has been applied either as the sole dye as in pure sulfur treatment or in a secondary dyeing operation as in a sulfur top treatment.

The oxidizing pretreatment step is conducted in a like manner to the aluminum salt treatment, but using a suitable oxidizing agent in an aqueous medium, preferably water. Suitable and preferred oxidizing agents include bromates such as sodium bromate, hydrogen peroxide, percarbonates such as sodium percarbonate, perborates such as sodium perborate, persulfates such a potassium persulfate and hydrates of the foregoing as well as mixtures of two or more of the foregoing. Hypochlorites such as sodium hypochlorite, also known as bleach, can be used but they are less preferred because they often have an adverse reaction with any dyes in the fabric. Sodium percarbonate is more preferred because it gives good results, is readily available and economical.

The concentration of oxidizer in water can vary but is preferably from about 0.05 to about 10% by weight. Lower levels are sometimes less effective and, when too low, ineffective and higher levels add unnecessarily to the cost. More preferably the concentration is from 0.1 to 7%, most preferably 0.2 to 5%. The contact time and temperature at which the pre-treatment is conducted is the same as for the aluminum treatment, as recited above.

Post Treatment Rinse

The second key step to the claimed process is that in which the fabric resulting from the aluminum salt treatment is rinsed with an aqueous medium, preferably water. In this step, the fabric is removed from the aluminum salt solution, either by draining the aluminum salt solution from the treatment vessel or by removing the treated fabric from the treatment vessel. In a preferred embodiment, especially from an economic and environmental standpoint, the fabric is subjected to wringing, spinning or centrifugation to remove excess solution from the fabric: the solution being added back to the original solution for reuse. Thereafter the fabric is rinsed one or more times, preferably with water. Preferably, the fabric is immersed in water, with or without agitation: immersion being attained by adding the fabric to a vessel of water or adding water to a vessel containing the fabric. Alternatively, one may use a spin rinse cycle, as in a consumer washing machine where water is sprayed as the fabric is spun using both water and centrifugal forces to wash or rinse the aluminum salt treatment solution from the fabric. Preferably, the aforementioned immersion technique is employed.

The amount of water to be used in the rinse step is typically from 1 to 500 times the weight of aluminum treated fabric. Lower amounts often do not give a sufficient rinse. Higher amounts are unnecessary and add to the cost. More preferably, the amount of water is from 2 to 250 times the weight of the fabric. Preferably, the rinse is done for 0.5 to 60 minutes, more preferably from 1 to 30 minutes. As noted above, the rinse can be done by passing water through the solid product or by a single immersion or a series of two or more immersions, with the second immersion in clean(er) water. When the amount of water to be used is on the lower end of the aforementioned range, immersion is preferred as the pass through method is not likely to fully remove the aluminum salt treatment which can lead to less than desired results in antimicrobial performance. Additionally, in the case of multiple immersions in a series of vessels, in order to save on water, one can discard the contents of the initial immersion vessel after a given number of batches of fabric have been rinsed and move the contents of the subsequent vessel to that vessel, doing the same for each subsequent vessel if applicable, and add fresh water to the last of the immersion vessels. Although not critical, it is preferred to wring, spin or centrifuge the rinsed fabric before moving to the next vessel to minimize carryover of the higher concentration aluminum salt. If a single immersion vessel is employed, it may be preferred to perform repeat the immersion rinse one or more times to ensure good removal of the aluminum salt. Most preferably, the rinse is done by immersion with agitation. Alternatively, one may also use a combination of rinse methods: performing an immersion to remove the majority of the aluminum salt solution followed by a spray rinse type method where water is passed through the fabric, much like the wash/spin cycle of a conventional washing machine. Following rinsing, the fabric is preferably subjected to wringing, spinning, or centrifugation in order to remove excess water and leave the fabric in a state where it will more readily absorb the antimicrobial agent solution.

Antimicrobial Treatment

The third key step of the present process is that in which the rinsed fabric is treated with an antimicrobial agent. Suitable antimicrobial agents are those that comprise antimicrobial metals and/or metal ions, especially those based upon or which readily release or generate metal ions through oxidation, degradation, ion-exchange, dissociation, solubilization, and the like: the latter collectively referred to as the "antimicrobial metal-ion type" antimicrobial agents.

Preferred antimicrobial metal-ion type antimicrobial agents include a) antimicrobial metal ion containing, ion-exchange agents; b) water soluble salts which, in the presence of water, dissociate to generate free antimicrobial metal ions and c) water soluble glass particles containing free antimicrobial metal ions or water soluble salts which, in the presence of water, dissociate to generate free antimicrobial metal ions: altogether. Antimicrobial metal ions include, but are not limited to, silver, copper, zinc, gold, mercury, tin, lead, iron, cobalt, nickel, manganese, arsenic, antimony, bismuth, barium, cadmium, chromium and thallium. However, given the intended end use applications, the preferred antimicrobial metal ions are silver, copper, gold, and zinc and combinations thereof. Silver ions, alone or in combination with copper or zinc or both, are more preferred due to the fact that they have the highest ratio of efficacy to toxicity, i.e., high efficacy to low toxicity, and are comparatively more cost effective than gold.

The antimicrobial agent can be in the form of a simple salt of the antimicrobial metal such as the oxide, sulfide, chloride, bromide, carbonate, nitrate, phosphate, dihydrogen phosphate, sulfate, oxalate, acetate, benzoate, thiosulfate and the like. Specific examples include silver nitrate, cupric oxide, cupric sulfate, copper acetate; silver acetate, and zinc acetate.

While the simple salts are effective, for applications where long term utility is desired and the substrate to which the composition is to be applied is to be subjected to washing, especially on a repeated basis, it is preferred that the antimicrobial agent be either a water soluble glass or an ion-exchange type agent. These agents are especially desired as they have and enable a much more controlled and timed release of the antimicrobial metal ion as opposed to the water soluble compounds. Alternatively, it may be desired to use a combination of the simple salts and the water soluble glass and/or the ion-exchange type agents whereby the former provides for a prompt, high level release of antimicrobial metal ion and, hence, performance and the latter a more moderate and longer lived antimicrobial metal ion release and, hence, a longer performance.

Antimicrobial water soluble glasses, especially the silver glasses, are commercially available, and are described in, e.g., Ishii et. al. —U.S. Pat. No. 6,831,028; Namaguchi et. al. U.S. Pat. No. 6,939,820; Nomura—U.S. Pat. No. 6,593,260; Shimono et. al. —U.S. Pat. Nos. 5,290,544 and 5,766,611; Gilchrist—U.S. Pat. No. 5,470,585 and US 20010006987 A1; Drake—U.S. Pat. No. 4,407,786; and Hikata et. al. —U.S. Pat. No. 6,410,633; which are incorporated herein by reference in their entirety. They are characterized as being similar to typical glasses except that the traditional glass former, silicon dioxide, is replaced, in whole or in part, with phosphorus pentoxide ($P_2O_5$) and/or boric oxide ($B_2O_3$) as a principal glass former. Other oxides employed, typically in combination with one or both of the foregoing, in forming water soluble glasses include, for example, CaO, $Na_2O$, MgO, $Al_2O_5$, ZnO, etc. Typically these compositions will have from about 35 to about 75 mole percent, preferably from about 40 to about 60 mole percent, of the phosphorous pentoxide or the boric oxide and from about 5 to about 55 mole percent, preferably from about 10 to about 40 mole percent, of another metal oxide, e.g., a Group IA or Group IIA metal oxide such as sodium oxide or calcium oxide, with silicon dioxide as the remaining or predominant remaining component Where both phosphorus pentoxide and boric oxide are present, the two in combination will account for from about 40 to about 85 mole percent, preferably from about 50 to about 80 mole percent, of the water soluble glass composition. Antimicrobial properties are achieved by incorporation of water-soluble, simple metal salts of silver and/or copper, such as silver oxide, silver acetate, cupric oxide, and copper acetate. These antimicrobial additives are typically incorporated into/present within the water soluble glass in the range of from about 1 to about 20%, preferably from about 3 to about 15%, by weight based on the total weight of the antimicrobial water soluble glass.

Antimicrobial water soluble glasses are available from a number of sources including Ishazuka Glass Co., Ltd., the latter selling silver glass under the tradename "Ionpure." Antimicrobial glasses dissolve and/or swell upon exposure to water, including, though more slowly, atmospheric moisture, thereby releasing or making available the antimicrobial metal ion source within the glass. By suitable adjustment of the glass composition, the dissolution rates in water can be controlled, thereby controlling the release of the antimicrobial metal ions and, hence, extending their longevity.

Alternatively, the antimicrobial agent may be in the form of an ion-exchange type antimicrobial agent or combinations of such agents. Ion-exchange type antimicrobial agents are typically characterized as comprising an ion-exchange capable ceramic particle having ion-exchanged antimicrobial metal ions, i.e., the antimicrobial metal ions have been exchanged for (replaced) other non-antimicrobially effective ions in and/or on the ceramic particles. While these materials may have some surface adsorbed or deposited metal, the predominant antimicrobial effect is as a result of the ion-exchanged antimicrobial metal ions released from within the ceramic particles themselves.

Antimicrobial ceramic particles include, but are not limited to zeolites, calcium phosphates, hydroxyapatite, zirconium phosphates and other ion-exchange ceramics. These ceramic materials come in many forms and types, including natural and synthetic forms. For example, the broad term "zeolite" refers to aluminosilicates having a three dimensional skeletal structure that is represented by the formula: $XM_{2/n}O$—$Al_2O_3$—$YSiO_2$—$ZH_2O$ wherein M represents an ion-exchangeable ion, generally a monovalent or divalent metal ion; n represents the atomic valence of the (metal) ion; X and Y represent coefficients of metal oxide and silica, respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

Generally speaking, the ion-exchange type antimicrobial agents used in the practice of the present invention are prepared by an ion-exchange reaction in which non-antimicrobial ions present in the ceramic particles, for example sodium ions, calcium ions, potassium ions and iron ions in the case of zeolites, are partially or wholly replaced with the antimicrobial metal ions, for example, copper and/or silver ions. The combined weight of the antimicrobial metal ions will be in the range of from about 0.1 to about 35 wt. %, preferably from about 1 to 25 wt. %, more preferably from about 2 to about 20 wt. %, most preferably, from about 2.5 to 15 wt. %, of the ceramic particle based upon 100% total weight of ceramic particle. Where the ceramic particles include two or more different antimicrobial metal ions, each antimicrobial metal ion is typically present in and amount of from about 0.1 to about 25 wt %, preferably from about 0.3 to about 15 wt. %, most preferably from about 2 to about 10 wt. % of the ceramic particle based on 100% total weight of the ceramic particle.

Although any of the above-mentioned antimicrobial metal ions may be employed, the preferred antimicrobial metal ions are zinc, copper and silver, as well as combinations of any two or all three. Where the fabric to be treated is a light colored fabric, either by its natural coloration or by dying, most especially if the fabric is white, it is preferred to use a combination of silver and copper ions, with or without zinc ions. In these instances, the weight ratio of silver to copper ions is from 1:10 to 10:1, preferably from 5:1 to 1:5, most preferably from 2.5:1 to 1:2.5. In an especially preferred embodiment, the ceramic particle contains from about 0.3 to about 15 wt. % of silver ions and from about 0.3 to about 15 wt, % of copper ions in a weight ratio of 5:1 to 1:5. Exemplary compositions are disclosed in Hendriks et. al. —US 2006/0156948A1 and 2008/0152905A1, both of which are incorporated herein by reference in their entirety.

The antimicrobial ceramic particles may also contain other ion-exchanged ions for various purposes, particularly ions that improve color stability of the fabrics and/or overall stability and/or ion release characteristics of ceramic particles. An exemplary and preferred other ion is ammonium ion. It is believed that ammonium ions aid in color stability of the substrates to which they are applied. These other ions, especially the ammonium ions, may be present at a level of up to about 20 wt. %, based on the total weight of the ceramic particle. Preferably, however, it is desirable to limit the content of ammonium ions to from about 0.1 to about 2.5 wt. %, more preferably from about 0.25 to about 2.0 wt. and most preferably from 0.5 to about 1.5 wt %, of the ceramic particles.

Antimicrobial silver hydroxyapatites are available from Sangi Company Ltd. of Tokyo. Japan under the tradename Apacider. These and other antimicrobial hydroxyapatite materials are made by a number of known processes including those disclosed in Sakuma et. al. —U.S. Pat. Nos. 5,009,898 and 5,268,174. Antimicrobial silver zirconium phosphates are available from Milliken Chemical Company of Spartenburg, S.C., US, under the tradename AlphaSan. These and other antimicrobial zirconium phosphates are made by a number of known processes including those disclosed in Tawil et. al. —U.S. Pat. No. 4,025,608: Clearfield—U.S. Pat. No. 4,059,679; Sugiura et. al. U.S. Pat. No. 5,296,238; and Ohsumi et, al. —U.S. Pat. Nos. 5,441,717 and 5,405,644, as well as in the Journal of Antibacterial and Antifungal Agents, Vol. 22, No. 10, pp. 595-601, 1994.

The preferred antimicrobial ion-exchange agents are the antimicrobial aluminosilicates, specifically the zeolites. A number of different grades and types of antimicrobial zeolites are commercially available from Sciessent, LLC of Wakefield, Mass., US under the Ag10N trademark. These include the following grades: AW10D—about 0.6% silver; AG10N and LG10N—about 2.5% silver; AJ10D—about 2.5% silver, 14% zinc, and 0.5%-2.5% ammonium ions; and AC10D—about 6.0% copper and about 3.5% silver: These are based on a type A zeolite of a mean average diameter of about 3µ, 10µ in the case of the LG grade. Such antimicrobial zeolites and their production are disclosed in, among others, Hagiwara et. al. —U.S. Pat. Nos. 4,911,898; 4,911, 899; and 4,775,585; Niira et. al. —U.S. Pat. Nos. 4,938,955 and 4,938,958; and Yamamoto et. al. —U.S. Pat. No. 4,906, 464.

It is to be appreciated that more than one antimicrobial agent may be employed in the practice of the present process. For example, two or more of the same type of antimicrobial agents may be used, e.g., two or more simple salts, two or more ion-exchanged zeolites, etc. Similarly, combinations of different antimicrobial agents may be used, e.g., a combination, of a water soluble glass and a zeolite or a combination of a simple salt and a zeolite. Additionally, where a plurality of sources of the antimicrobial metal ions are employed, one may provide one or more specific metal ions and the other another one or more specific metal ions. Alternatively, where it is desired to have two different ions, one of which is in excess of the other, e.g., the combination of silver and copper as noted above, one may use a silver salt in combination with a silver/copper zeolite. All such iterations are within the scope of the present teachings.

While the aforementioned antimicrobial agents are typically employed in their neat form, i.e., as the salt or particle, it is also contemplated that they may be employed in an encapsulated form wherein discrete particles of each are individually coated with a hydrophilic material or a plurality of particles of each or, in the case of multiple antimicrobial agent, of the combination are dispersed in discrete particles of a hydrophilic material. Of course, in both cases, it is also contemplated that only one component of the antimicrobial agent be encapsulated and the other employed in its neat form.

In one preferred embodiment, the antimicrobial agent is encapsulated in a hydrophilic polymer. The hydrophilic polymer used to encapsulate the antimicrobial agent is a polymer that can absorb sufficient water to enable the encapsulated particle to exhibit good antimicrobial behavior, i.e., to allow for the migration and release of the antimicrobial active agent. The polymer will be characterized by having water absorption at equilibrium of at least about 2% by weight measured by ASTM D570. Preferably, the polymer will have a water absorption capacity at equilibrium of at least about 5% by weight. More preferably, the polymer will have water absorption at equilibrium of at least about 20% by weight Especially suitable hydrophilic polymers include those having water contents of from about 50 and to about 150% by weight.

Typically the polymeric compositions useful as the encapsulating material are those which include substantial quantities of monomers having polar groups associated with them, such that the overall polymeric composition is rendered hydrophilic. The polar groups can be incorporated into the polymer main chain as in, for example, polyesters, polyurethanes, polyethers or polyamides. Alternatively or in addition, the polar groups can be pendant to or grafted onto the main chain as in for example, polyvinyl alcohol, polyacrylic acids or as in ionomers such as Surlyn®. Surlyn® is available from Dupont and is the random copolymer poly(ethylene-co-methacrylic acid) wherein some or all of the methacrylic acid units are neutralized with a suitable cation, commonly $Na^+$ or $Zn^{+2}$. While not being limited by way of theory, it is believed that the inclusion of polar groups allows water to more readily permeate the polymer and consequently, to allow slow transport of the metal ion through the encapsulating polymer layer.

Exemplary hydrophilic polymers useful as the encapsulating material include, but are not limited to, (poly)hydroxyethyl methacrylate, (poly)hydroxypropyl methacrylate, (poly)glycerol methacrylate, copolymers of hydroxyethyl methacrylate and methacrylic acid, polyacrylamide, hyaluronan, polysaccharides, polylactic acid, copolymers of lactic acid, (poly)vinyl pyrrolidone, polyamides such as Nylon 6,6 or Nylon 4,6 or Nylon 6,12, cellulosics, polyureas, polyurethanes and certain polyesters containing a high percentage (at least about 10% by weight, preferably at least about 25% by Weight or more) of polyalkylene oxide. The hydrophilic polymer may be a copolymer containing at least a substantial amount of at least one or more of the above-mentioned hydrophilic monomers, including, for example, styrene/methacrylic acid/hydroxyethyl methacrylate copolymers, styrene/methacrylic acid/hydroxypropyl methacrylate copolymers, methylmethacrylate/methacrylic acid copolymers, ethyl methacrylate/-styrene/methacrylic acid copolymers and ethyl methacrylate/methyl methacrylate/styrene/methacrylic acid copolymers, copolymers based upon the cellulosics, and copolymers which utilize vinylpyrrolidone monomers, among numerous others.

Other hydrophilic polymers that may be used to encapsulate the antimicrobial metal ions include polyvinyl acetate, polyvinyl alcohol, and copolymers of polyvinyl alcohol and polyvinylacetate, polyvinylchloride, copolymers of polyvinylacetate and polyvinylchloride and hydroxyl-modified vinyl chloride/vinyl acetate copolymers. Polyurethanes containing a high percentage (at least about 10% by weight, preferably at least about 25% by weight or more) of polyalkylene oxide are especially useful to encapsulate the antimicrobial metal ions. Methods of encapsulation are described in U.S. Pat. No. 7,357,949, incorporated herein by reference.

The amount of encapsulating material will vary widely depending upon the intended application and, more importantly, the type of encapsulation employed. In the case of individually encapsulated antimicrobial particles, the microcapsule will typically have a coating thickness of up to 15µ of hydrophilic polymer; preferably a coating thickness of 1 to 10µ. While thicker coatings could be used efficaciously, concern must then be given to the impact, if any, of the presence of the hydrophilic polymer on the properties of the matrix resin into which the encapsulated particles and the speed with which the antimicrobial metal ions are able to release from the particles. In the case of microcapsules containing multiple antimicrobial particles, the microcapsules will typically have a mean average diameter of up to and over 2000µ, but generally not over 3000µ; preferably from about 15 to about 1000µ, more preferably from about 50 to about 300µ, most preferably from about 90 to about 200µ, Here; concern is not only given to the speed and efficiency in which the antimicrobial metal ions are able to release from the particles, but to the overall feel of the fabric into which they are applied. Larger particles will have a sand-paper type effect resulting in both a rough feel as well as a shortened life for the fabric owing to constant rubbing of the particles against the fiber or fibril strands which may cause premature wear and compromise the overall strength and other properties of the fabric. Exemplary encapsulated antimicrobial materials and their methods of manufacture are described in Trogolo et. al. —U.S. Pat. No. 7,357,949, which is incorporated herein by reference.

The antimicrobial agent, whether encapsulated or not, may be applied by any of the methods known in the art, including dusting, spraying, brushing, rolling, printing; dipping and the like. The exact method will depend, in part, upon a number of variables such as the type of antimicrobial agent employed; the type of fabric to be treated, whether a binder is employed or not, etc. Regardless of which method is employed, the antimicrobial will preferably be applied so as to provide from 0.05 g to 2 g antimicrobial metal, preferably from 0.1 to 1 g antimicrobial metal, more preferably from 0.2 g to 0.6 g antimicrobial metal, per meter of fabric. Lower levels are often insufficient to impart good antimicrobial efficacy and higher levels, though perhaps providing more immediate and a higher level of efficacy, are often unnecessary and add to the cost. From a commercial perspective, one preferably balances the cost of the material with the speed and degree of performance warranted. For example, one may use a lower loading or amount of antimicrobial agent in the case of run-of-the-mill socks and underwear available are one's low end consumer retail store and a higher loading in the same type of products, though now a designer brand, sold through a high end, premium retail store. Similarly, disposable and/or limited life garments may employ lower levels of the antimicrobial agent since longevity of efficacy is not an issue.

As noted, there are multiple ways by which the antimicrobial agent is applied to the fabric. For example, one may apply the antimicrobial agent as a dry powder, either dusting the fabric or combining the two and then subjecting the dusted or combined materials to tumbling and other mechanical action whereby the particles become entrapped in the weave and/or interstitial spaces in the fabric. Similarly, the antimicrobial agent may be applied as a suspension, dispersion or like composition in a suitable, neutral solvent to the fabric or combined with the fabric and then subjected to agitation where, again, the antimicrobial agent becomes entrapped in the weave and/or interstitial spaces in the fabric as the solvent evaporates leaving the antimicrobial agent in place. The neutral solvent, which may be water or an aqueous based liquid, e.g., water-alcohol solution, is one that does not affect the fabric and merely carries the antimicrobial agent before evaporating off. These methods, while effective are less desirable as retention of the antimicrobial agent is reliant upon mechanical entrapment and subsequent washing will tend to lead to the dislodgement and loss of the entrapped particles.

Alternatively, a suspension, dispersion or like composition of the antimicrobial agent in a suitable, volatile solvent may be applied to the fabric except here the solvent is one that causes a swelling or softening of the composition of the fabric. In this manner, the particles of the antimicrobial agent become bonded, embedded and/or impregnated into the swelled or tackified surface layer of the fabric and is deposited or affixed thereto once the solvent evaporates and the swelling and/or tackiness subsides.

Preferably, the antimicrobial agent is applied by treating the fabric with a coating composition comprising the antimicrobial agent and a binder. The coating composition may be a 100% solids based composition or a "solvent" based system such as true solutions, dispersions or colloids. 100% solid compositions are flowable compositions that cure or set upon exposure to the atmosphere or other curing conditions. While avoiding the environmental, health and safety concerns associated with the use of solvents, 100% solids binder compositions oftentimes suffer from higher viscosity and, therefore, can be more difficult to employ with textiles, especially where the intent is to get a thin even coating of the antimicrobial agent on the textile surface without adding bulk to the individual fibers or filaments or the textiles as a whole.

Binder systems are well known and are currently used for altering and/or providing other textile modifiers to the surfaces of textiles. Especially suited binders are commonly referred to as finishing agents for the textile industry. While it appears that the preferred binders are those based on polyurethanes or acrylics, especially anionic or lightly anionic acrylics, in practice essentially any effective cationic, anionic, or non-ionic binder resin may be used. Most preferably, the binder resin is non-ionic or slightly anionic. Suitable non-ionic binders include those based on polyurethane such as those available from BASF under the tradename Lurapret as well as binder resins selected from the group consisting of non-ionic permanent press binders (i.e., cross-linked adhesion promotion compounds) including, without limitation, cross-linked imidazolidinones such as those available from Sequa under the tradename Permafresh. Anionic and slightly anionic binders include various acrylics, such as Rhoplex TR3082 from Rohm & Haas and those sold by BASF under the tradename Helizarin. Other potential binder resins include, but are not limited to melamine formaldehyde, melamine urea, ethoxylated polyesters (such as Lubril QCX from Rhodia), and the like. Oftentimes there binders will also contain other surfactants, leveling agents and the like. Preferred binder systems are those having an aqueous or aqueous-based carrier or solvent.

Typically the binder system will comprise from about 0.1 to about 60 weight percent, most preferably from about 1 to about 40 weight percent of the antimicrobial agent based on the total weight of binder composition or system. The amount of each component of the antimicrobial agent and the ratio thereof in the solidified binder resin will be as set forth above. These antimicrobial binder systems may also contain one or more co-constituents for modifying or altering the textile surface or properties. For example, the antimicrobial binder system may further include UV or thermal stabilizers, adhesion promoters, leveling agents, odor absorbing agents, sizing agents, thickeners and the like. Each will be present in their traditional amounts for the particular textile or end-use application thereof.

The antimicrobial binder systems may be applied by any of the methods known in the art, including spraying, brushing, rolling, printing, dipping and the like. Typically these antimicrobial binder systems will be applied so as to provide as thin a coating as possible while concurrently providing the needed degree of antimicrobial performance. Such rate of applications will be consistent with the manufacturer stated or art recognized rate of application for the neat (i.e., without antimicrobial agent) binder or finishing system. Most preferably, the rate of application will be such as to provide from about 0.01 to 20 weight percent, preferably from about 0.02 to 10 weight percent antimicrobial binder system based on the combined weight of the binder system and textile.

While the foregoing discussion has been on the basis that antimicrobial agent is incorporated into the binder system, those skilled in the art will also recognize that the antimicrobial agent and binder system may be applied to the fabric in two separate steps according to two different methodologies. In the first, the fabric is first wetted with the binder system and the antimicrobial agent dusted onto the wetted surface. The antimicrobial agent essentially resides on the outer surface of the subsequently cured or hardened binder resin. Alternatively, the surface of the fabric may be dusted with the antimicrobial agent and then the dusted surface treated with the binder system: thereby encapsulating or potting the particles of the antimicrobial agent to the textile surface.

Based on the foregoing general discussion of the steps and materials employed in the practice of the present teachings, it is to be appreciated that the process may involve a number of different elements and iterations. For example, the process may be conducted in a single vessel in which the fabric is immersed in each of the respective solutions and/or compositions. Alternatively the vessel could be of the type that allows for a continuous or intermittent spray of the solutions or compositions while the fabric is being tumbled, agitated and/or spun. A single vessel may be capable of both actions, as with a commercial/-consumer washing machine. While such single vessel batch method is suitable for small scale processes, larger scale processes will preferably employ a plurality or series of vessels, each dedicated to a single or perhaps two of the steps of the process or, as also noted above, a single step may employ a plurality of vessels, especially the rinse step. To assist in such a process, the fabrics could be placed in a basket that is lowered into each vessel and then retracted once the processing in that vessel is completed. Preferably, this basket would be capable of spinning to add centrifugal forces to the fabric so as to effectively spin out the liquids. In this case, the vessel may be of such depth that the basket is raised from the liquid, without removal of from the vessel, and spun so that the effluent from the spinning remains in the vessel and falls back into the bulk of the liquid. Generally speaking, those skilled in the art, with the benefit of the above described teachings will readily appreciate the multitude of various systems that could be devised to maximize the efficiency of the process for the particular need of the person or entity employing the same.

The present teachings also provide for an antimicrobial fabric, preferably one having both antimicrobial and anti-odor characteristics. The present teachings especially provide for antimicrobial fabrics derived or made from sulfur-containing fabrics, particularly those treated by the method of the invention. This is especially beneficial and surprising inasmuch as, up to now, it has been difficult, if not impossible, or nearly so, to impart suitable antimicrobial activity to sulfur-containing fabrics. It has been especially difficult to have any permanence to the antimicrobial activity when the sulfur-containing fabrics are subjected to repeated washings. In particular, the present teachings provide antimicrobial efficacy, preferably to at least a one log reduction, preferably a two log reduction, most preferably a three log reduction in, e.g., staph aureus and/or klebsiella pneumoniae after 20 washings, preferably after 30 washings as measured by AATCC 100. The current invention solves this problem. Fabrics prepared by the method of this invention enhance and expand the many and varied uses of sulfur-containing fabrics.

The following examples merely illustrate the invention. Those skilled in the art will recognize many variations that are within the spirit of the invention and scope of the claims.

Example 1

A series of evaluations of the claimed method were performed on 10" by 12" samples of dyed denim fabric. The samples evaluated were indigo dyed (ID), sulfur tops (ST—indigo dyed and then sulfur dye), sulfur bottom (SB—sulfur dye and then indigo dye) and pure sulfur (PS—no indigo dye). Each sample was placed in a 1 L flask containing 325 g of an aqueous solution of 7% by weight aluminum sulfate. The contents were agitated for 45 minutes on a laboratory shaker. The fabric is then removed from the flask and agitated in a pail for five minutes with 3 L of water at 35° C. The water is drained, 3 L of fresh water at 35° C. is added and the mixture agitated for five minutes. The fabric is removed and agitated in a pail for ten minutes with a solution of 3 g sodium carbonate in 3 L of water at 35° C. The solution is drained, 3 L of fresh water at 35° C. is added and the mixture agitated for five minutes. The fabric is removed and dried for 45 minutes in a clothes dryer set at high. The fabric is placed in a tumbling cylinder and a solution of an aqueous acrylic based binder system containing 20% by weight of a 60:40 combination of silver/copper zeolite (grade AC10D available from Sciessent LLC, Wakefield, Mass.): silver/zinc zeolite (grade AJ100 available from Sciessent LLC, Wakefield, Mass.) is metered in by spraying as a mist over a period of about ten minutes to give a loading of 0.3 g combined metal per square meter of fabric. Following application, the fabric is heated for 3.5 minutes at 150° C. to dry the fabric and cure the binder.

Portions of each sample were then washed 30 times in a standard washing machine set at regular wash setting with three ounces of Tide laundry detergent. The antimicrobial efficacy of the washed and unwashed samples was then determined in accordance with the Dow Shaker Test (ASTM E2149). Specifically, approximately a 0.5 g sample of each fabric was placed in an individual receptacle containing 25 mL of an inoculum buffer having $1.09 \times 10^5$ CFU/mL of staphylococcus aureus (staph a.), as determined by plate count enumeration. The receptacles were placed on a shaker and maintained at room temperature for 24 hours. An organism count was then made of the original inoculum as well as the inoculum from the samples and the percent reduction (based on the original inoculum) determined. In similar fashion antimicrobial efficacy was tested using kleb. pneumoniae (kleb p.) as well. The specific tests and the results attained thereby are presented in Table 1.

The results shown in Table 1 demonstrate the marked and surprising improvement in antimicrobial performance with those fabric samples which have undergone the aluminum treatment.

Example 2

10" by 12 samples of denim were treated in a similar fashion to the samples in Example 1, but using different concentrations and duration as well as different levels of the antimicrobial treatment. Following application, the amount of available antimicrobial metal ion was evaluated by soaking the fabric and determining the metal ion content of the solution. The results are presented in Table 2.

TABLE 1

| Fabric | AM | AlSO$_4$ | Staph a. (% reduction) | | Kleb p. (% reduction) | |
| --- | --- | --- | --- | --- | --- | --- |
| | | | 0 wash | 30 wash | 0 wash | 30 wash |
| ID | Yes | Yes | 99.998 | 99.998 | 99.999 | 99.999 |
| ID | No | No | No reduc. | | No reduc. | |
| SB | Yes | Yes | 99.998 | 99.95 | 99.999 | 99.99 |
| SB | No | No | No reduc. | | No reduc. | |
| ST | Yes | Yes | 99.91 | 87.24 | 99.999 | 98.07 |
| ST | No | Yes | | 51.03 | | 72.14 |
| ST | No | No | No reduc | | No reduc | |
| PS | Yes | Yes | 99.89 | 69.41 | 99.999 | 27.5* |
| PS | No | No | No reduc. | 66.76 | No reduc. | 32.5 |

*Sample was contaminated

TABLE 2

| AlSO$_4$ | | | Ag (ppb) | Cu (ppb) |
| --- | --- | --- | --- | --- |
| Concentration | Time | AM* | 0 wash | 0 wash |
| 10% | 5 min | 0.4 | 370 | 430 |
| 10% | 80 min | 0.4 | 210 | 260 |
| none | | 0.4 | 12 | 21 |
| 1% | 5 min | 0.3 | 68 | 52 |
| 4% | 5 min | 0.3 | 70 | 94 |
| none | | | 4 | 8 |
| 5% | 45 min | 0.3 | 180 | 380 |

*~weight of antimicrobial metal per square meter of material

The results presented in Table 2 demonstrate the marked improvement in the retention of the antimicrobial metal treatment with those fabric samples which have been subjected to the aluminum treatment.

Example 3

A second series of evaluations of the claimed method were performed on 2"×2" samples of denim pant legs, this time adding a sodium percarbonate pretreatment. The pant legs evaluated were indigo dyed (ID), sulfur tops (ST—indigo dyed and then sulfur dye) and sulfur bottom (SB—sulfur dye and then indigo dye). Before subjecting the pant legs to the present process, the pant legs were desized with amylase enzymes and stonewashed. The same test procedure was then performed, as follows, on four samples of each pant leg.

As a pretreatment, each pant leg was placed in a Unimac dying machine and containing 30 liters of a 1.6% aqueous solution of sodium percarbonate at 45° C. for 20 minutes. The pant legs were then removed from the sodium percarbonate solution and washed with clean water 2× at about 40° C. The pant legs were then submerged in a 6% aqueous solution (~30 liters) of aluminum sulfate hydrate at 45° C.

for 20 minutes (approx. pH of 3.5). The pant legs were then removed from the aluminum sulfate solution and washed with clean water 2× at about 40° C. (approx. pH 4.0). The pant legs were then subjected to centrifugation to remove excess water, bringing the water content down to about 60%. The antimicrobial treatment from Example 1 was then applied using a Tonello machine by spray 10 seconds on, 20 seconds off, to apply approximately 0.4 grams of metal ion per square meter of fabric; however, the indigo samples without the sodium percarbonate/aluminum sulfate treatment received double the volume of the antimicrobial solution, ~0.8 grams/meter$^2$, Finally, the treated pant legs were dried. The treated and untreated samples were then subjected to antimicrobial performance evaluations in accordance with AATCC100 using Staph aureus as the test organism, both before and after 30 washes, 24 hour contact. The test samples and results are presented in Table 3, where the individual results represent the average of the four test samples.

TABLE 3

| Fabric | NaPer/AlSO$_4$ | AM | Staph a. (% reduction) 0 wash | 30 wash |
|---|---|---|---|---|
| ID | No | No | No reduc. | No reduc. |
| ID | No | Yes | 99.9998 | 99.99 |
| ID | Yes | Yes | 99.9999* | 99.997 |
| SB | Yes | Yes | 99.9998 | 99.99 |
| ST | Yes | Yes | 99.88 | 99.9 |

*one sample contaminated and ignored

The results shown in Table 3 demonstrate the longevity of the performance of the antimicrobial agent, even with washing. Although the performance benefit between the sodium percarbonate/aluminum sulfate pretreatment and those not subjected to the pretreatment appears minimal in a percent reduction standpoint, any reduction in terms of bacteria is important.

Example 4

The experiment of Example 3 was repeated with samples of sulfur bottoms; however, following the washing before application of the antimicrobial agent, the fabric was dried so that the wet antimicrobial composition was applied to a wet fabric. In this instance, at zero washings the treatment provided a 99.999% reduction and a 99.96 reduction after 30 washings.

Example 5

A series of experiments were conducted in accordance with the procedure set forth in Example 3 to show the impact of the percarbonate pretreatment. Each sample was treated with the 6% aluminum sulfate solution and the 0.4 g/m$^2$ antimicrobial application. In this example, the sodium percarbonate solution, if used, was reduced to a 0.9% concentration. Additionally, the microbiological testing was conducted with two test organisms, S. aureus and Kleb. pneumoniae. The test samples and the results, the average of two test results, are shown in Table 4.

TABLE 4

| Fabric | NaPer | Staph a. (% reduction) 0 wash | 30 wash | Kleb p. (% eduction) 0 wash | 30 wash |
|---|---|---|---|---|---|
| ST | No | No reduc. | 80 | No reduc. | 87.6 |
| ST | Yes | 86.5 | 23 | 78.9 | 94.9 |
| SB | No | 83.1 | 96.9 | 98.1 | 97.4 |
| SB | Yes | 99.6 | 99.96 | 99.995 | 99.9995 |

The results presented in Table 4 clearly show the benefit of the added carbonate pretreatment.

Although the process and prepared articles of the present specification have been described with respect to specific embodiments and examples, it should be appreciated that the present teachings are not limited thereto and other embodiments utilizing the concepts expressed herein are intended and contemplated without departing from the scope of the present teaching. Thus the true scope of the present teachings is defined by the claimed process steps and any and all modifications, variations, or equivalents that fall within the spirit and scope of the underlying principles set forth herein.

I claim:

1. A method for treating a sulfur-containing fabric, said method comprising the following steps in the order presented:
   a) treating the fabric with an aluminum salt solution comprising an aluminum salt capable of sequestering, binding and/or reacting with sulfur and sulfur-containing species;
   b) rinsing the treated fabric with water or another suitable solvent to remove the aluminum salt from the fabric to give a rinsed fabric; and
   c) treating the rinsed fabric with an antimicrobial metal-ion type antimicrobial agent.

2. The method of claim 1 further comprising the step of treating the sulfur-containing fabric with an aqueous solution of an oxidizing agent prior to or concurrent with the treatment of the fabric with the aluminum salt.

3. The method of claim 2 wherein the oxidizing agent is selected from hydrogen peroxide, percarbonates, bromates, chlorates, persulfates, perborates, and hydrates thereof and combinations thereof.

4. The method of claim 2 wherein the oxidizing agent is a hydrate of sodium percarbonate.

5. The method of claim 1 wherein the sulfur-containing fabric has been treated with a sulfur dye.

6. The method of claim 1 wherein the sulfur-containing fabric has been treated with a combination of indigo and a sulfur dye.

7. The method of claim 1 wherein the sulfur-containing fabric is denim.

8. The method of claim 1 wherein the sulfur-containing fabric is apparel made from denim.

9. The method of claim 1 wherein the sulfur-containing fabric is wool.

10. The method of claim 1 wherein the aluminum salt contains an anion selected from sulfate, carboxylate, phosphate, and hydroxide.

11. The method of claim 1 wherein the aluminum salt is a hydrate.

12. The method of claim 10 wherein the aluminum salt is selected from aluminum sulfate and hydrates of aluminum sulfate.

13. The method of claim 1 wherein the antimicrobial agent is used at a level to provide from 0.05 g to 1 g antimicrobial metal per meter$^2$ of fabric.

14. The method of claim 1 wherein the antimicrobial agent is used at a level to provide from 0.2 g to 0.6 g antimicrobial metal per meter$^2$ of fabric.

15. The method of claim 1 wherein the antimicrobial agent is a source of silver ions and copper ions and the weight ratio of silver ions to copper ions is from 1:10 to 10:1.

16. The method of claim 1 wherein the antimicrobial agent is an ion-exchange type antimicrobial agent having both ion-exchanged silver and copper ions.

17. The method of claim 16 wherein the ion-exchange type antimicrobial agent is a zeolite having ion-exchanged silver and copper ions.

18. The method of claim 1 wherein the antimicrobial agent is applied together with or in combination with a binder system for binding the antimicrobial agent to the fabric.

19. A process for improving the antimicrobial and/or anti-odor performance of fabric whose antimicrobial and/or anti-odor efficacy depends, in whole or in part, upon the release, presence or generation of antimicrobial metal ions said process comprising:
   a) treating the fabric with an aluminum salt solution comprising an aluminum salt capable of sequestering, binding and/or reacting with sulfur and sulfur-containing species inherently, including naturally, present in the fabric and/or imparted to the fabric though some process and/or treatment thereof which otherwise inhibit the release or generation of, complex with, sequester, bind and/or react with antimicrobial metal ions, and then
   b) rinsing the treated fabric with water or another appropriate solvent to remove the aluminum salt, before
   c) treating the rinsed fabric with an antimicrobial metal-ion type antimicrobial agent.

20. The method of claim 1 wherein
   a) the aluminum salt solution is an aqueous solution having a concentration of from 0.1 to 30% by weight, or
   b) the fabric is treated with the aluminum salt solution for a period of from 1 minute to 2 hours, or
   c) the amount of water used in the rinse is from 1 to 500 times the weight of the treated fabric, or
   d) the rinsing with water is performed for from 0.5 to 60 minutes, or
   e) the rinse step involves more than one rinse cycle or
   f) any two or more of (a), (b), (c), (d) and (e).

21. The method of claim 2 wherein the concentration of the oxidizing agent is from 0.05 to 10% by weight of the aqueous solution.

* * * * *